(12) United States Patent
Kelkar et al.

(10) Patent No.: US 11,253,432 B1
(45) Date of Patent: Feb. 22, 2022

(54) SYSTEMS, METHODS, ASSEMBLIES, AND COMPONENTS FOR MEDICATION REMINDERS

(71) Applicants: Praful K. Kelkar, Medina, MN (US); Rituraj Chauhan, Maple Grove, MN (US)

(72) Inventors: Praful K. Kelkar, Medina, MN (US); Rituraj Chauhan, Maple Grove, MN (US)

( * ) Notice: Subject to any disclaimer, the term of this patent is extended or adjusted under 35 U.S.C. 154(b) by 0 days.

(21) Appl. No.: 16/751,103

(22) Filed: Jan. 23, 2020

Related U.S. Application Data

(60) Provisional application No. 62/825,546, filed on Mar. 28, 2019, provisional application No. 62/795,978, filed on Jan. 23, 2019.

(51) Int. Cl.
| | | |
|---|---|---|
| *G08B 1/08* | (2006.01) | |
| *A61J 7/04* | (2006.01) | |
| *G06F 3/14* | (2006.01) | |
| *G08B 21/24* | (2006.01) | |
| *H04B 1/40* | (2015.01) | |
| *G16H 20/10* | (2018.01) | |
| *B33Y 80/00* | (2015.01) | |
| *A61J 1/03* | (2006.01) | |
| *G16H 40/20* | (2018.01) | |
| *G16H 10/60* | (2018.01) | |
| *G16H 40/67* | (2018.01) | |

(52) U.S. Cl.
CPC ............... *A61J 7/0481* (2013.01); *A61J 1/03* (2013.01); *B33Y 80/00* (2014.12); *G06F 3/14* (2013.01); *G08B 21/24* (2013.01); *G16H 20/10* (2018.01); *H04B 1/40* (2013.01); *G16H 10/60* (2018.01); *G16H 40/20* (2018.01); *G16H 40/67* (2018.01)

(58) Field of Classification Search
CPC ........... A61J 7/0481; A61J 1/03; G08B 21/24; B33Y 80/00; G06F 3/14; G16H 20/10; G16H 40/67; G16H 40/20; G16H 10/60; H04B 1/40
USPC .............................. 340/539.1, 573.1, 309.16
See application file for complete search history.

(56) References Cited

U.S. PATENT DOCUMENTS

| | | | | |
|---|---|---|---|---|
| 7,017,513 | B2 * | 3/2006 | Giewercer | ............ G09F 11/04 116/308 |
| 9,795,198 | B1 * | 10/2017 | Krieger | ..................... G09F 3/02 |
| 10,380,327 | B1 * | 8/2019 | Bradley | ................. G06F 3/147 |
| 2005/0183982 | A1 * | 8/2005 | Giewercer | ............ B65D 83/04 206/534 |

(Continued)

*Primary Examiner* — Anh V La
(74) *Attorney, Agent, or Firm* — Fantastic IP Consulting; Eduardo E. Drake

(57) ABSTRACT

To address the widespread problem of half of all patients failing to take prescribed medications as directed by their physicians, the present inventor devised, among other things, one or more medication reminders. For example, one embodiment, particularly suitable for only two- or three-a-day prescriptions, comprises a repositionable indicator mechanism that attaches via a self-adhesive microsuction backing to the top or other surface of a plastic prescription medication bottle. The indicator, which can take the form of a slider that moves between two or three indicator positions, in some cases using a detent locking mechanism, to simultaneously indicate the prescribed dosage frequency, last dosage taken, and remaining dosages for a day.

7 Claims, 7 Drawing Sheets

(56) References Cited

U.S. PATENT DOCUMENTS

| | | | |
|---|---|---|---|
| 2006/0139150 A1* | 6/2006 | Brue | A61J 7/0481 340/309.16 |
| 2014/0007806 A1* | 1/2014 | Stanton | G09F 3/08 116/201 |
| 2014/0130453 A1* | 5/2014 | Shalala | B65B 7/28 53/420 |
| 2015/0148947 A1* | 5/2015 | McConville | G16H 20/13 700/244 |
| 2016/0199261 A1* | 7/2016 | Morgan | A61J 7/0481 368/10 |
| 2017/0169185 A1* | 6/2017 | Weng | G06Q 10/1093 |
| 2017/0228519 A1* | 8/2017 | Chu | G08B 25/10 |
| 2018/0250196 A1* | 9/2018 | Warden | A61J 1/18 |

* cited by examiner

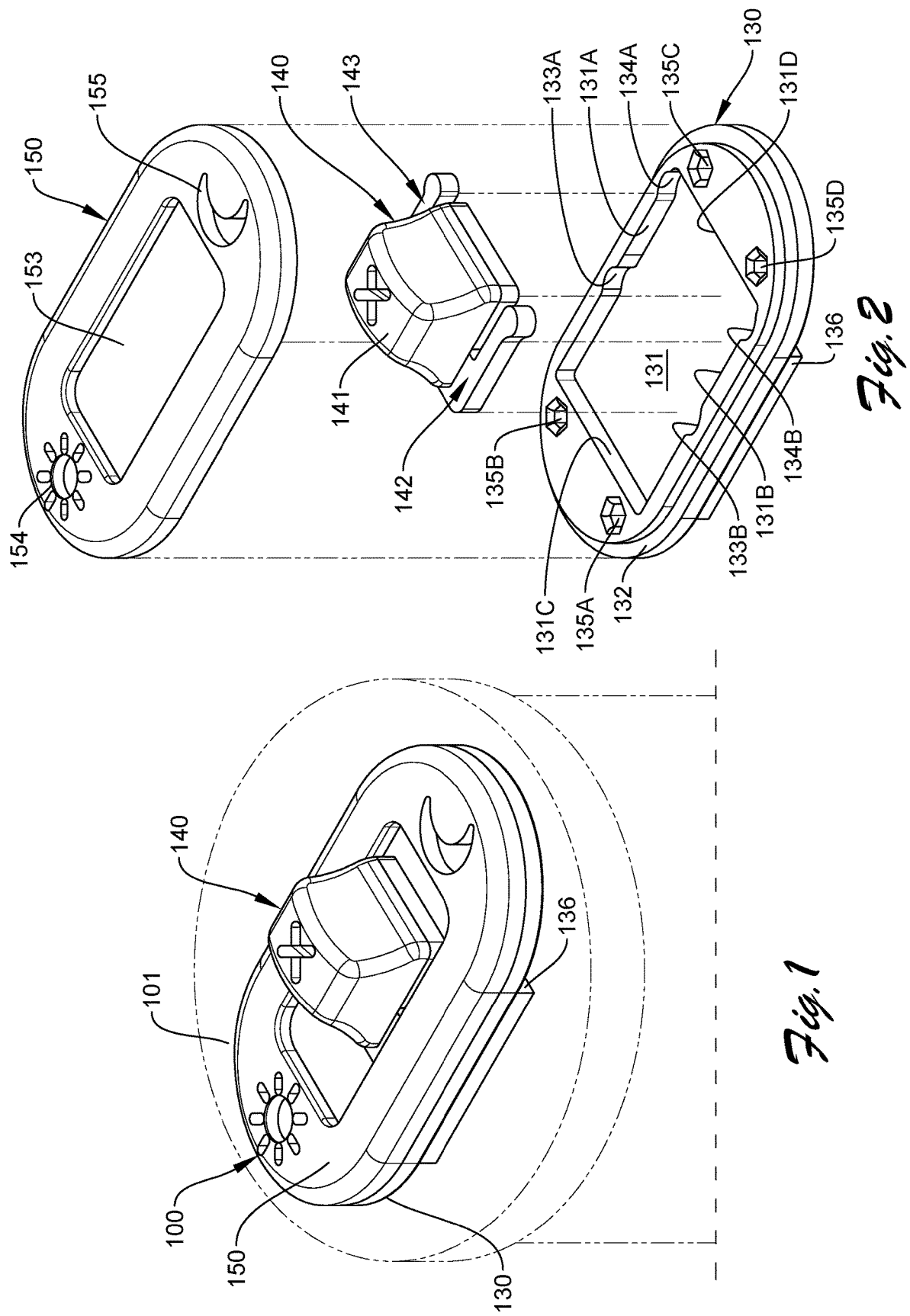

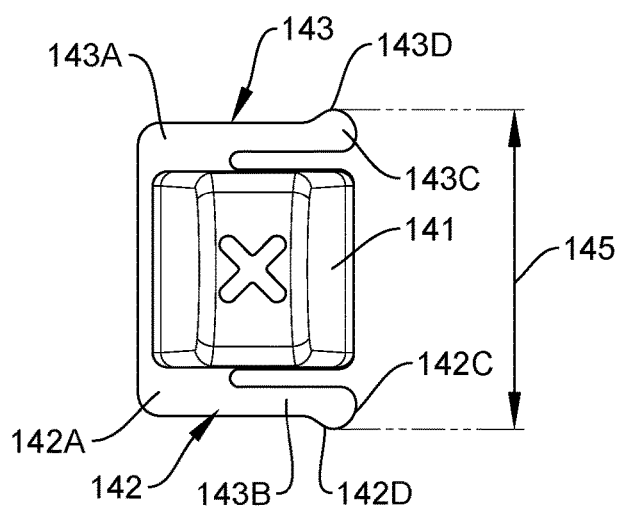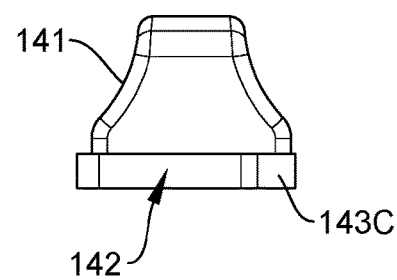
Fig. 4A　　　Fig. 4B
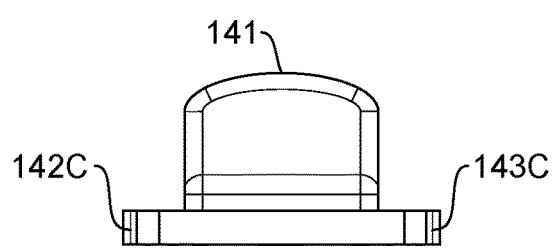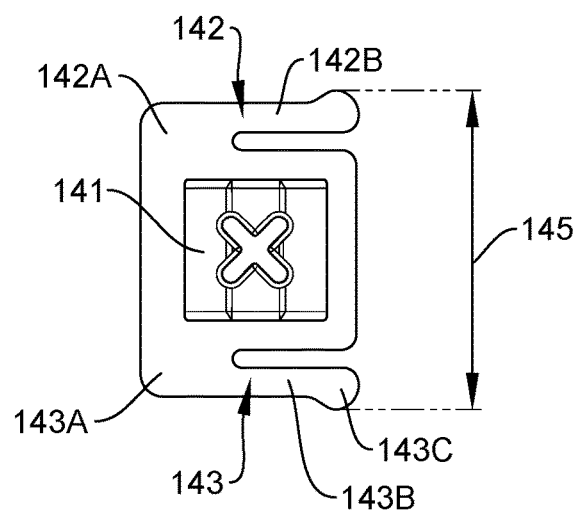
Fig. 4C　　　Fig. 4D

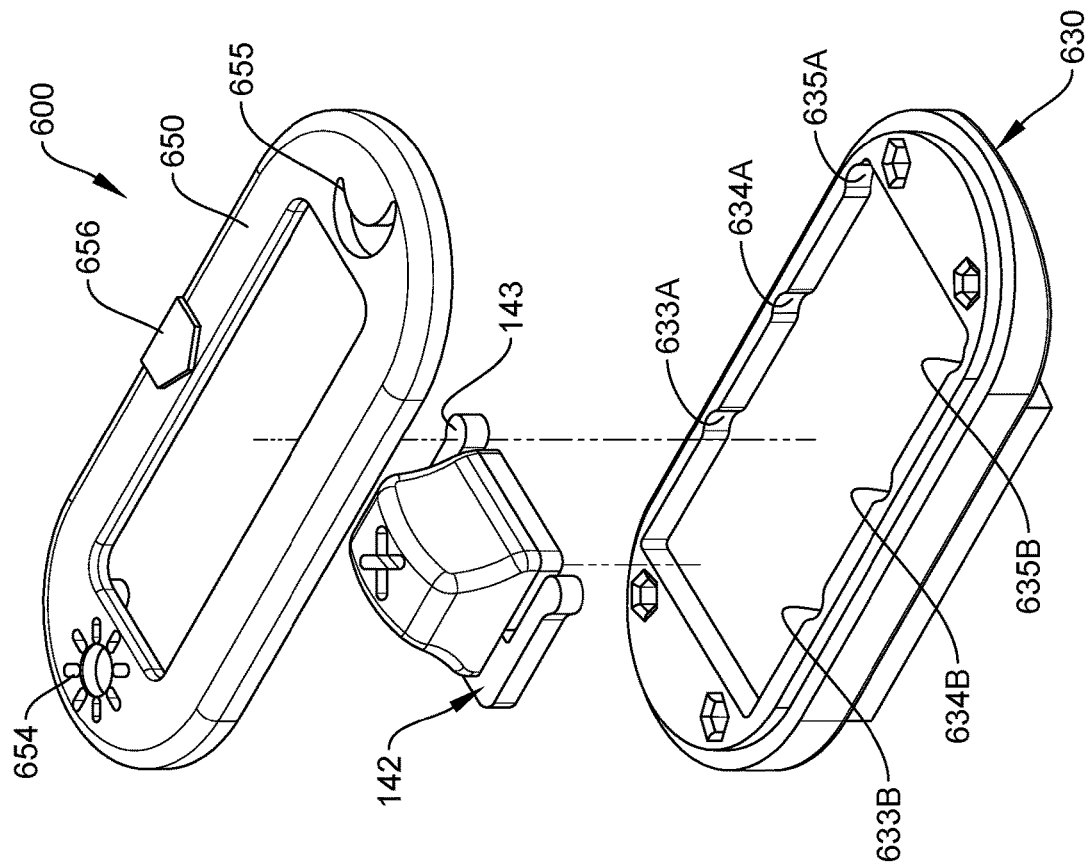
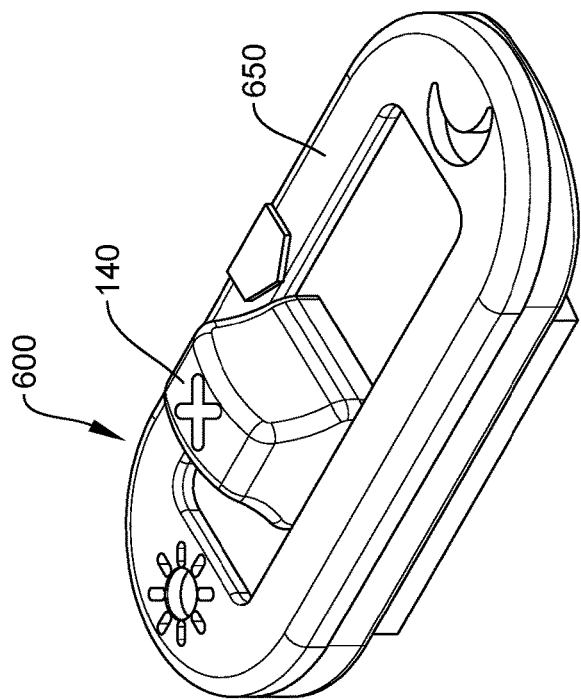

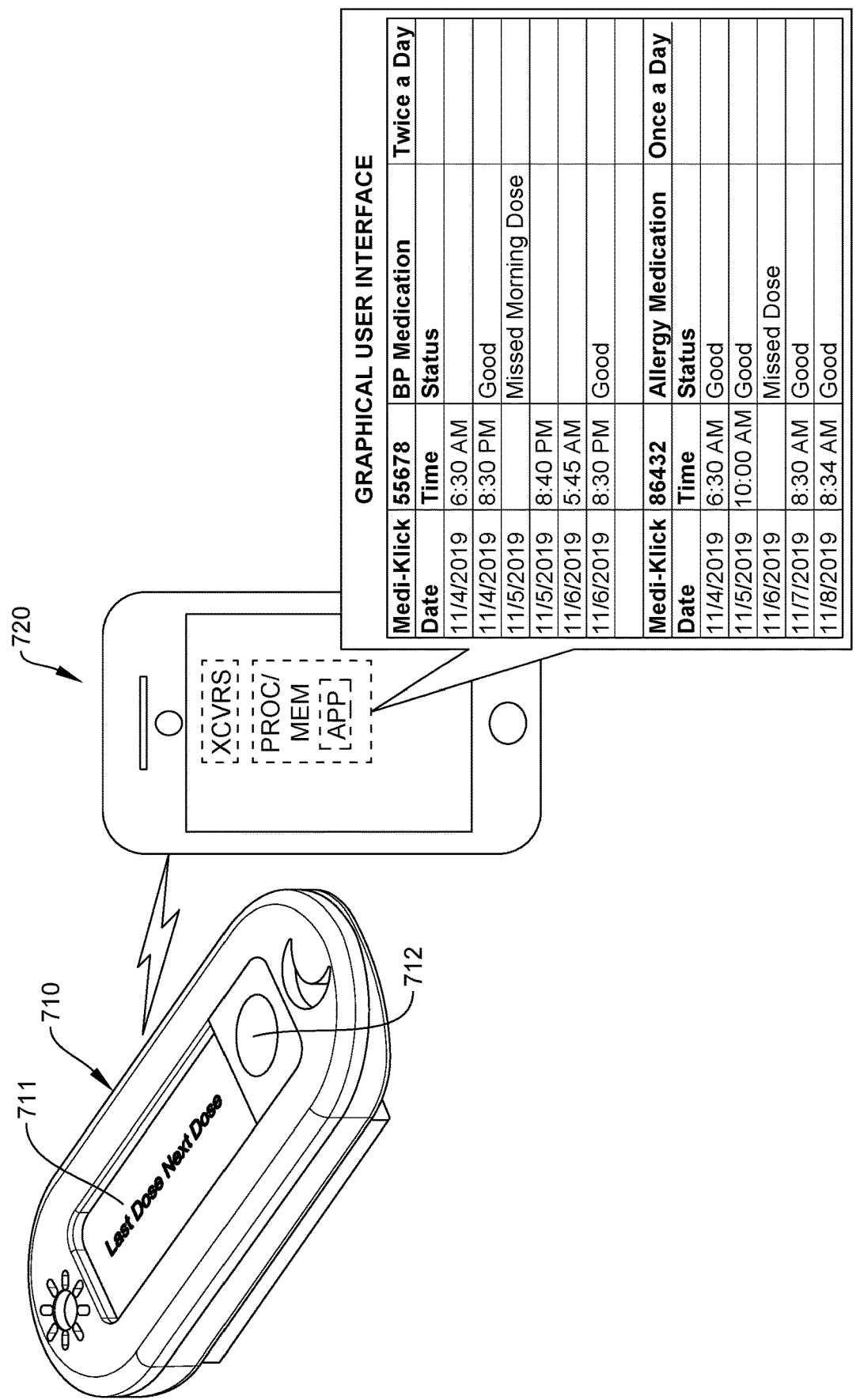

SYSTEMS, METHODS, ASSEMBLIES, AND COMPONENTS FOR MEDICATION REMINDERS

RELATED APPLICATIONS

This application claims priority to U.S. Provisional Patent Applications 62/795,978 filed Jan. 23, 2019 and 62/825,546 filed Mar. 28, 2019. Both these applications are incorporated herein by reference in their entirety.

COPYRIGHT NOTICE AND PERMISSION

A portion of this patent document contains material subject to copyright protection. The copyright owner has no objection to the facsimile reproduction by anyone of the patent document or the patent disclosure, as it appears in the patent and trademark office patent files or records, but otherwise reserves all copyrights whatsoever. The following notice applies to this document: Copyright © 2019, PRAFUL M. KELKAR.

TECHNICAL FIELD

Various embodiments of the invention relate generally to prescription medication reminders.

BACKGROUND

Prescription medication is one of the foundations of the American healthcare system. According to a Mayo Clinic study, 70% of Americans are taking prescription medication to promote their wellbeing. Unfortunately, others studies have revealed that about 50% of people prescribed medications do not take them as prescribed, evidencing the broad scope of a healthcare problem known as "medication non-adherence" (MNA). Recent estimates are that MNA generates about $300 billion in avoidable healthcare costs and leads to 125,000 preventable deaths each year.

Over the years a multitude of medication reminders ranging from multi-day pill trays to electronically programmable bottles and dispensers have been devised to combat the problem. Generally speaking, they are complicated, cumbersome, costly, and/or difficult to use, and have therefore failed to significantly curtail the number of avoidable deaths and high financial costs of MNA. Accordingly, there remains a long-standing and dire need for better medication reminders, particularly reminders that are not only simple, affordable and easy to use, but also work well with existing medication bottles, boxes, and other common medication containers.

SUMMARY

To address one or more of these and/or other needs or problems, the present inventor devised, among other things, one or more exemplary systems, kits, methods, devices, assemblies, and components related to, among other things, medication reminders (as well as other types of reminders, sensors, and/or switches). For example, one exemplary embodiment comprises a repositionable indicator mechanism that attaches via a self-adhesive backing to the top or other surface of a plastic prescription medication bottle. (Some embodiments may use a microsuction, magnetic, or hook-and-loop fastener arrangement.) The indicator, which can take the form of a slider moves between two or three indicator positions to simultaneously indicate the prescribed dosage frequency, last dosage taken, and remaining dosages for a day. For example, the mechanism may have two positions for two-a-day prescription or three regions for three-a-day prescription. (The most common prescriptions are for once, twice, or thrice daily. Patients often cannot remember if they took a particular dose or not, particularly when a medication is to be taken more than once a day. This results in either not taking the proper dose or doubling the dose of the medication.) The slider or dial is moved manually from one region to the next with each consumed dosage of the medication, thus indicating the number of dosages taken and the number remaining for the day.

In some embodiments, a generally planar plastic housing sandwiches the indicator and the resilient locking or detent member between upper and lower housing portions, thereby generally constraining movement of the indicator and resilient member to a single plane between the upper and lower portions. In some embodiments, the upper and lower housing are formed by separate pieces that snap or are glued together, whereas in other embodiments, the upper and lower portions are integrally molded or 3D printed together as a single piece having a living hinge between them, allowing one to fold the upper portions over and onto the lower portion.

BRIEF DESCRIPTION OF DRAWINGS

Various embodiments are described herein with reference to the following attached figures (Figs). These figures are annotated with reference numbers for various features and components, and these numbers are used in the following description as a teaching aid, with like numbers referring to the same or similar features and components.

FIG. 1 is a perspective view of a two-dose exemplary attachable medication reminder, corresponding to one or more embodiments of the invention;

FIG. 2 is an exploded perspective view of the FIG. 1 medication reminder, corresponding to one or more embodiments of the invention;

FIGS. 4A, 4B, 4C, and 4D are respective top, side, front, and bottom view of a slide indicator button portion of the attachable medication reminder, corresponding to one or more embodiments of the invention;

FIGS. 6A and 6B are respective perspective and exploded perspective views of an attachable three-dose medication reminder, corresponding to one or more embodiments of the invention;

FIG. 7 is a perspective view of medication reminder system including an active medication reminder and a smartphone/computer, corresponding to one or more embodiments of the invention;

DESCRIPTION OF EXEMPLARY EMBODIMENT(S)

Figure 3A:
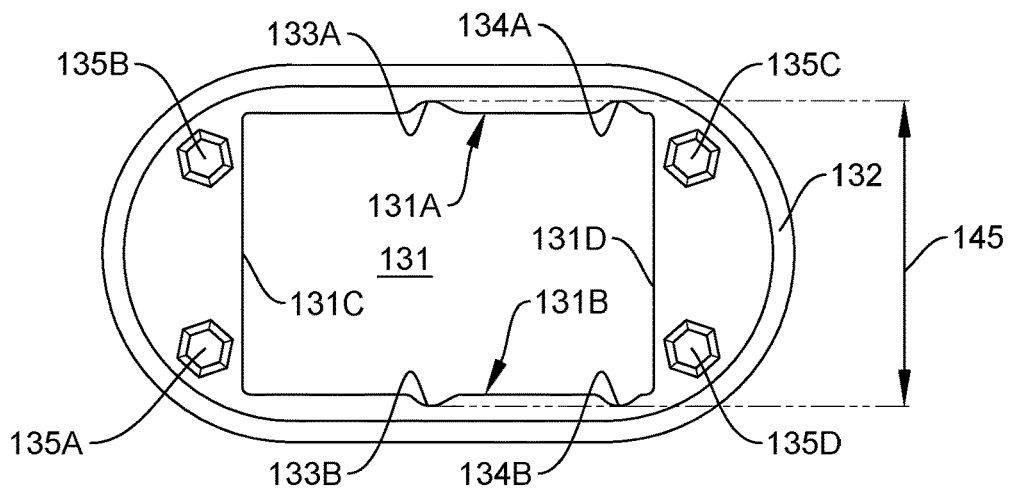
FIGS. 3A, 3B, 3C, and 3D are respective top, side, sectional, and bottom views of a base portion of the attachable medication reminder, corresponding to one or more embodiments of the invention.
Figure 3B:
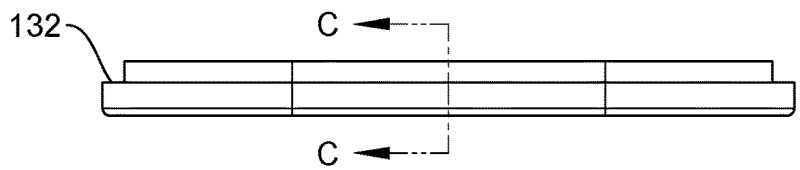
Figure 3C:
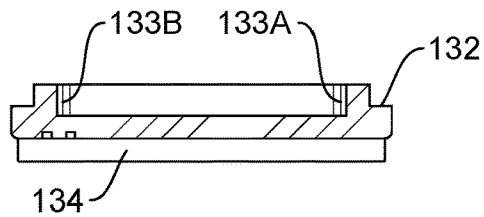
Figure 3D:
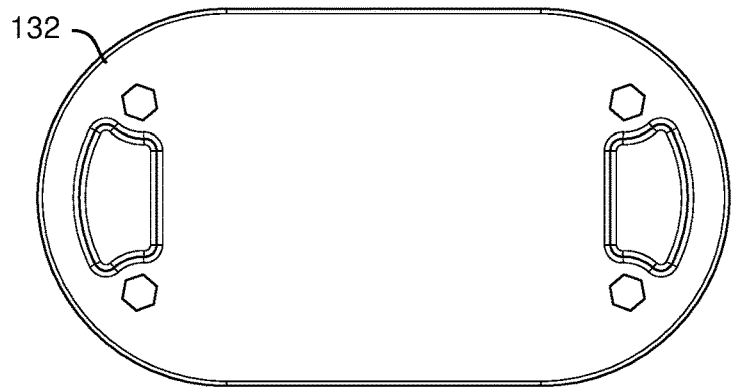
Figure 5A:
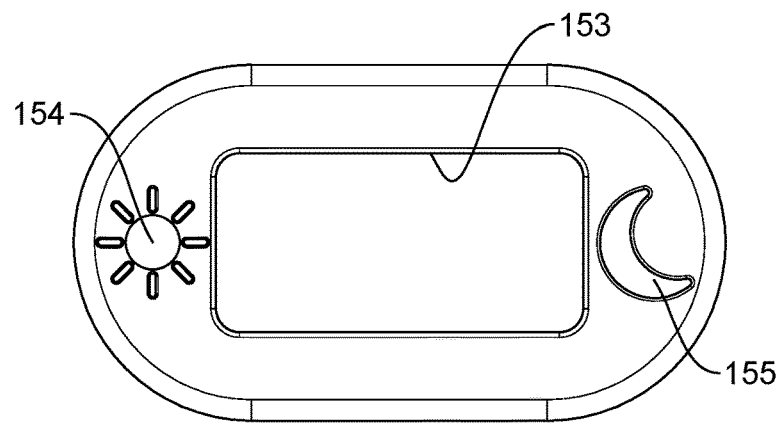
FIGS. 5A, 5B, 5C, and 5D are respective top, side, sectional, and bottom views of a top portion of the attachable medication reminder, corresponding to one or more embodiments of the invention.
Figure 5B:
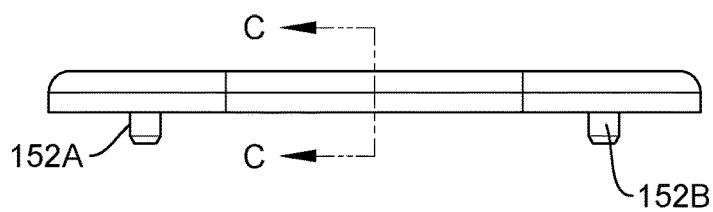
Figure 5C:
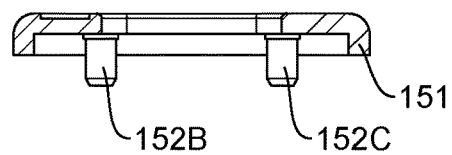
Figure 5D:
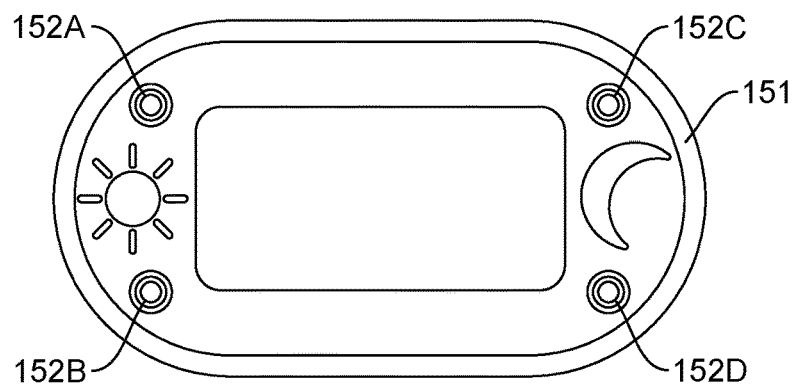

This document, which incorporates drawings and claims, describes one or more specific embodiments of one or more inventions. These embodiments, offered not to limit but only to exemplify and teach the invention, are shown and described in sufficient detail to enable those skilled in the art to implement or practice the invention(s). Thus, where appropriate to avoid obscuring the invention(s), the description may omit certain information known to those of skill in the art.

FIG. 1 shows an exemplary embodiment of a two-dose attachable medication reminder 100 attached to a medication or supplement container 101. Reminder 100 is shown in greater detail in the exploded view of FIG. 2, and in the views of its principle components parts 130, 140, and 150 in FIGS. 3A-3D, 4A-4D, and 5A-5D. Reminder 100 includes a base portion 130 which is attached to a medication or supplement container 101, a slide indicator button 140 which is slidable operated by a user, and a top portion 150, which retains slider indicator button in place and provides prescription and dosage status indicia.

More particularly, base portion 130, having a flat oval shape and including a central rectangular recess 131, an outer peripheral ledge 132, notches or detents 133A,133B, 134A,134B, post holes 135A-135B, and fastening device 136. Recess 131 includes opposing parallel sidewalls 131A and 131B, and opposing parallel sidewalls 131C and 131D, which are transverse (for example perpendicular) to sidewalls 131A and 131B. Sidewall 131A includes arcuate notches or detents 133A and 134A, and sidewall 131B includes arcuate notches or detents 133B and 134B. Notches 133A and 133B are directly opposite each other, defining a first slide lock position relative to sidewalls 131C and 131D. Similarly, notches 134A and 134B are disposed opposite each other and thus equi-distant from sidewall 131C and 131D. Post holes 135A-135B are configured to receive top posts 152A-152D in top portion 150 (FIGS. 5A-5D). Fastening layer 136 takes the form of a self-adhesive layer adhered to a surface of the container after removal of disposable release liner (not shown). In some embodiments, the fastening layer takes the form of a micro-suction tape, magnetic layer, and/or hook-and-loop fastener. Some embodiments integrally mold the base portion into the child-proof medication cap.

Configured for sliding engagement with sidewalls 131A and 131B is slide indicator button 140, shown more particularly in FIGS. 4A-4D. Slide indicator button 140 includes a bulbous central button portion 141 and integrally molded opposing side spring arms 142 and 143. Spring arms 142 and 143 include respective shoulder regions 142A and 143A, respective straight intermediate arm regions 142B and 143B, and rounded follower end regions Shoulder regions 142 and 143 extend outwardly, for example perpendicularly, from back regions of opposing sidewalls 141A and 141B of button portion 141, and intermediate arm regions 142B and 143B extend forwardly from their corresponding shoulder regions, parallel to and spaced from sidewalls 141A and 142, terminating into respective rounded follower regions 142C and 143C. Follower regions 142C and 143C include respective rounded or convex faces 142D and 143D which are configured to engage with the sidewalls 131A and 131B as slider button 140 moves forward or backward in a direction parallel to sidewalls 131A and 131B. The distance between convex faces 142D and 143D is selected to be substantially the same as or slightly greater than (for example +/−2-5%) that between the outermost portions of opposing notches 132A and 133A, and the outermost portions of notches 132B and 133B, such that movement of the slider button parallel to sidewalls 131A and 131B from a locked position within the A or B notches forces the spring arms together until the convex faces 142D and 143D engage with another set of opposing notches, allowing the spring arms to return to a neutral or more relaxed state than without engagement of the notches. (In some embodiments, the notches are omitted altogether and the friction between the arms and sidewalls and/or between the arms and the surfaces contacting the top and base portions inhibit free movement of the slider button between the indicia.) Overlying the spring arms to restrict vertical movement of slider button 140 is top portion 150.

Top portion 150, also shown more particularly in FIGS. 5A-5D, includes a peripheral sidewall 151, mounting posts 152A-152D, slider window 153, and prescription indicia regions 154 and 155. Peripheral sidewall 151 mates flush and in snap-fit engagement with peripheral ledge 132, and posts 152A-152D engage in an interference or snap-fit with respective post holes 135A-135B, securing top portion 150 to base portion 130 and sandwiching the spring arms of slider button 140 therebetween. In some embodiments, the top and base are fastened using an adhesive in conjunction with or in lieu of the posts and holes and sidewall and ledge joints. Slider window 143, which takes a rectangular form in this embodiment, fits around slider indicator button 140, defining together with sidewalls 131A and 131B a path for movement of the button between indicia regions 154 and 155. In the exemplary embodiment, indicia region 154 takes the form of a sun icon cut out of the surface at one end of top portion 150, exposing a portion of base 130, which in some embodiment may have a different or contrasting color from that of the adjacent portion of top 150. Indicia region 155, at the opposite end of top 150, takes the form of a moon or lunar icon cut out of the surface at one end of top portion 150. In some embodiments, the indicia are embossed, printed, or adhered to the top.

In this exemplary embodiment, there are only two indicia provided on the top portion to indicate that the medication or supplement in the associated container is to be taken twice daily, once in the morning and once in the evening, for example. Additionally, the position of the slider button in closer proximity to one indicia or other, for example, via user engaging the slider button with his or her thumb or index finger, indicates that the last dose taken was in the evening or in the morning and conversely that the next dose (or other action) to be taken is for the time period of the indicia farthest from the slider button.

FIGS. 6A and 6B, perspective and exploded perspective views, show an attachable three-dose medication reminder 600, similar in basic form and function to reminder 100, with the exception that reminder 600 provides an extended base 630 and extend top 650 to indicate a three-times daily prescription and status information as to the last dose taken and the next dose to be taken. In particular, extended base 630 includes a rectangular recess having three pairs of opposing notches or detents 633A, 634A, 633B, 634B, and 635C, 635C to engage with and lock slide indicator button 140 in place relative to corresponding first, second, and third indicia 654, 655, and 656. These indicia may correspond respectively to morning, midday, and evening or night time dosages.

Some embodiments provide an alternative top for reminder 600 that provides only two indicia and prevents travel of the slider indicator button to the third indicia. This would allow for packaging of base portion 630, slider indicator button 140, and top portions 650 and the travel-limited version of 650 together so that a user could configure the reminder for use with two- or three-times daily medications or supplements. Moreover, in some contexts, it would reduce the need for a mold for the twice daily base, and thus reduce manufacturing and inventory cost. Note that some embodiments of the invention include 4 or more pairs of opposing detents and notches and corresponding indicia regions for counting and reminding users regarding 4 or more doses.

FIG. 7 shows an attachable active medication reminder system 700, which includes an attachable reminder device 710 communicatively coupled via a wireless link, for example a Bluetooth, Wi-Fi, or NearField Communication compatible link, to a smartphone or tablet computer 720. Reminder device 710 is similar in outward form factor as reminders 100 and 600; however, unlike devices 100 and 600, device 710 includes an electronic display 711 for indicating a date/time of last taken dose and/or date/time of next dose is due and an input button or switch 712 for accepting manual user indication that a dosage of medication or supplement has been taken. In some embodiments, all or a portion of the display is a touch-screen display, obviating need for a separate button. Some embodiments may also use an electronic ink display to extend useful battery life, since such displays only consume power upon changing display. In some embodiments, the display and button are recessed below the uppermost surface of top portion 650 to protect from inadvertent physical contact. Also, in some embodiments, programmable visual and/or audible reminder alerts, with snoozing functionality is provided.

Figure 8:
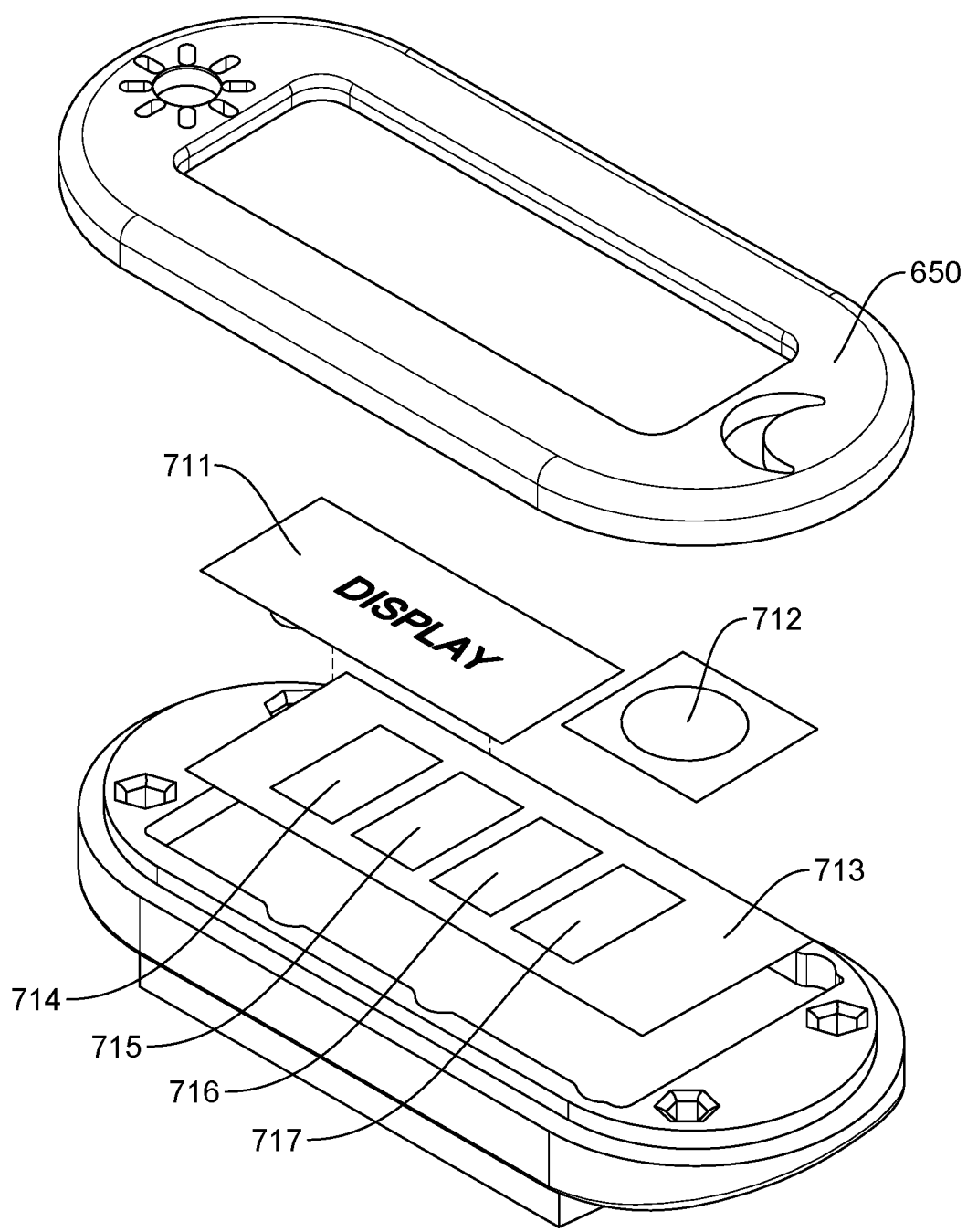
FIG. 8 is an exploded perspective view of the FIG. 7 reminder, corresponding to one or more embodiments of the invention.

FIG. 8, an exploded view, shows that reminder 710 additionally includes a printed circuit board 713 with a processing circuitry module 714 (with on-board clock), a memory 715, a wireless transceiver circuitry module 716, and a rechargeable battery circuitry module 717, enabling the reminder device to not only store medication dosage history date/time stamps and display next dosage data that is computed based on dosage frequency and date/time of last taken dose, but also receive and transmit data to and from smartphone 720. In some embodiments, the data incudes a device identity and/or security access code, medication ID code, dosage frequency (one, two, three, or four times daily) and reminder parameters. Memory 715, for example a flash memory, stores date/time dosage was taken, counter data, Unique ID of the board, medication name with unique ID.

In some embodiments, memory 715 also includes machine executable instructions in the form on iOS or Android compatible app, for providing a configuration, data collection, and data reporting functionality. In some embodiments, the configuration functionality includes the following: pairing the phone or tablet to reminder device 710 via Bluetooth communications; assigning medication to a specific reminder device (including picking medications from a local or remote database of medications along with listing of benefits and side effects); specifying dosage as once a day, twice a day, thrice a day or four times a day (including prompting user to call physician to double check prescription or dosage if the medication is contradicted by other prescribed medications or user medical conditions, or typical prescriptions practices for the medication, for example duration of use); pairing multiple reminder devices to respective medications/supplements; re-assigning medicine already assigned to one reminder device to another reminder device. Exemplary Data Collection entails reading (interrogating) one or more reminder devices and saving data locally on the smartphone or tablet and/or to a remote server or other devices, such an medical records repository. Exemplary reporting entails generating simple on-screen report tables indicating: reminder Device ID (or nickname), medicine name, date/time medication taken, missed doses. Additionally, some embodiments provide systems integration capabilities, including ability to export data from phone or tablet to Excel, CSV, or human readable format, and ability to output the data in multiple Health Care System formats for easy import or upload to EMR repository of one or more health clinics or hospital systems, or even health and life insurance companies.

CONCLUSION

In the foregoing specification, specific exemplary embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms, such as second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed. Also, the term "exemplary" is used as an adjective herein to modify one or more nouns, such as embodiment, system, method, device, and is meant to indicate specifically that the noun is provided as a non-limiting example.

What is claimed is:

1. A medication reminder assembly comprising:
  a housing including upper and lower portions and at least one travel path feature, with the upper portion of the housing having an outer surface having only two spaced temporal indicia to indicate a twice daily dosage frequency and the travel path feature fixed relative to the two indicia and associated with at least one detent region positioned on the lower portion of the housing and hidden by the upper portion of the housing when fully assembled;

an indicator positioned at least partly outside the housing to move along the path toward or away from one of the two spaced temporal indicia;

a resilient indicator lock attached to the indicator and movable to engage with the at least one detent region to selectively lock the indicator in a first position along the path to indicate one of the two indicia; and wherein the lower portion of the housing includes a rectangular recess, the recess having an interior sidewall that defines at least a portion of the path feature and that includes the at least one detent region integrally molded therein.

2. A medication reminder assembly comprising:

a housing including upper and lower portions and at least one travel path feature, with the upper portion of the housing having an outer surface having only three spaced temporal indicia to indicate a thrice daily dosage frequency and the travel path feature fixed relative to the three indicia and associated with at least one detent region positioned on the lower portion of the housing and hidden by the upper portion of the housing when fully assembled;

an indicator positioned at least partly outside the housing to move along the path toward or away from one of the three spaced temporal indicia;

a resilient indicator lock attached to the indicator and movable to engage with the at least one detent region to selectively lock the indicator in a first position along the path to indicate one of the only three indicia; and wherein the lower portion of the housing includes a rectangular recess, the recess having an interior sidewall that defines at least a portion of the path feature and that includes the at least one detent region integrally molded therein.

3. A medication reminder system comprising:

a housing at least partially attachable to a medicine container and at least partially enclosing an electronic display coupled to a processing circuit, a memory coupled to the processor circuitry, a wireless transceiver circuit coupled to the processor circuitry, and a battery coupled to the display, the memory, and the wireless transceiver circuitry, wherein the processor is configured via executable code stored in the memory to display a last dosage taken time stamp and a next dosage due time indicator, and further configured to wirelessly communicate with a smartphone; wherein the system further comprises a-self-adhesive backing means for removably attaching the housing to a lid portion of a medicine container; and a smartphone having a display, a processor, and a memory associated therewith, wherein the memory is configured with machine-executable instructions to cause display of a graphical user interface including first and second listing regions for respective first and second different medications, with each listing region including an associated medication identifier identifying the type of first and second medication, two or more date stamps indicating date and time that its associated medication was deemed to be taken, and with at least one of the listing regions including a date associated with a missed dose indication.

4. A medication reminder assembly comprising:

a housing including upper and lower portions and at least one travel path feature, with the upper portion of the housing having an outer surface having a set of two or more spaced temporal indicia to indicate a dosage frequency and the travel path feature fixed relative to the set of indicia and associated with at least one detent region positioned on the lower portion of the housing and hidden by the upper portion of the housing when fully assembled;

an indicator positioned at least partly outside the housing to move along the path toward or away from at least of the set of indicia;

a resilient indicator lock attached to the indicator and movable to engage with the at least one detent region to selectively lock the indicator in a first position along the path to indicate one of the set of indicia; and wherein the lower portion of the housing includes a rectangular recess, the recess having an interior sidewall that defines at least a portion of the path feature and that includes the at least one detent region integrally molded therein.

5. The assembly of claim 4: wherein the resilient indicator lock has a thickness and wherein the indicator includes a bulbous portion having an uppermost portion extending above the resilient indicator lock by at least an amount at least twice the thickness.

6. The assembly of claim 4, wherein at least one of the indicia is formed as an opening through the outer surface of the housing.

7. The assembly of claim 4, wherein the travel path includes first and second end portions defining a maximal length of the path, and at least one of the indicia is position beyond the first and second end portions.

* * * * *